(12) United States Patent
Nicolas et al.

(10) Patent No.: US 10,694,784 B2
(45) Date of Patent: Jun. 30, 2020

(54) CARTRIDGE AND A SYSTEM FOR AN AEROSOL-FORMING ARTICLE INCLUDING THE CARTRIDGE

(71) Applicant: PHILIP MORRIS PRODUCTS S.A., Neuchatel (CH)

(72) Inventors: Frederic Nicolas, Moret sur Loing (FR); Rui Nuno Batista, Morges (CH)

(73) Assignee: Philip Morris Products S.A., Neuchatel (CH)

(*) Notice: Subject to any disclaimer, the term of this patent is extended or adjusted under 35 U.S.C. 154(b) by 285 days.

(21) Appl. No.: 15/758,424

(22) PCT Filed: Sep. 1, 2016

(86) PCT No.: PCT/EP2016/070589
§ 371 (c)(1),
(2) Date: Mar. 8, 2018

(87) PCT Pub. No.: WO2017/042081
PCT Pub. Date: Mar. 16, 2017

(65) Prior Publication Data
US 2018/0255833 A1 Sep. 13, 2018

(30) Foreign Application Priority Data
Sep. 11, 2015 (EP) .................................... 15184800

(51) Int. Cl.
*A24F 47/00* (2020.01)
*A24F 40/30* (2020.01)
(Continued)

(52) U.S. Cl.
CPC ............ *A24F 47/008* (2013.01); *A24F 40/30* (2020.01); *A24F 40/42* (2020.01); *A61M 15/06* (2013.01)

(58) Field of Classification Search
CPC .................................. A24F 40/30; A24F 40/42
(Continued)

(56) References Cited

U.S. PATENT DOCUMENTS

2005/0016550 A1\* 1/2005 Katase .................. A24F 47/002
131/194
2011/0084094 A1\* 4/2011 Reidt ................... A61C 9/0026
222/137
(Continued)

FOREIGN PATENT DOCUMENTS

WO WO 2014/110119 7/2014
WO WO 2015/038981 3/2015
(Continued)

OTHER PUBLICATIONS

PCT Search Report and Written Opinion for PCT/EP2016/070589 dated Oct. 27, 2016 (12 pages).

*Primary Examiner* — Joseph M Pelham
(74) *Attorney, Agent, or Firm* — Meuting Raasch Group

(57) ABSTRACT

The present invention relates to a cartridge (10), comprising: An outer shell (20) defining an inner volume containing: A first reservoir (30) containing a first component and having a first aperture (32) for discharge of the first component; a second reservoir (40) containing a second component and having a second aperture (42) for discharge of the second component; A first removable film (34) impermeable to the first component sealing the first aperture; A second removable film (44) impermeable to the second component sealing the second aperture; A seat (12) having an opening (14) in said outer shell and delimiting walls within said inner volume, said first and second apertures being formed in said delimiting walls, the seat being configured to house a piercer (50) of an external component; and Wherein a portion of the first film or a portion of the second film is protruding from said opening or it faces said opening. The present invention
(Continued)

also relates to a system for an aerosol-forming article (1000) and to a method for opening a cartridge in an aerosol-forming article.

17 Claims, 4 Drawing Sheets

(51) Int. Cl.
*A24F 40/42* (2020.01)
*A61M 15/06* (2006.01)

(58) Field of Classification Search
USPC .......................................................... 392/404
See application file for complete search history.

(56) References Cited

U.S. PATENT DOCUMENTS

| | | | |
|---|---|---|---|
| 2014/0060527 A1* | 3/2014 | Liu | A61M 15/06 128/202.21 |
| 2017/0144827 A1* | 5/2017 | Batista | A61M 15/06 |
| 2017/0181472 A1* | 6/2017 | Batista | A24F 47/008 |
| 2018/0029782 A1* | 2/2018 | Zuber | A24F 47/008 |
| 2018/0168231 A1* | 6/2018 | Reevell | A61M 15/0003 |
| 2018/0169357 A1* | 6/2018 | Reevell | A61M 11/042 |
| 2018/0228216 A1* | 8/2018 | Saygili | A24B 15/167 |

FOREIGN PATENT DOCUMENTS

| | | |
|---|---|---|
| WO | WO 2015/101651 | 7/2015 |
| WO | WO 2015/197627 | 12/2015 |
| WO | WO 2016/156212 | 10/2016 |

* cited by examiner

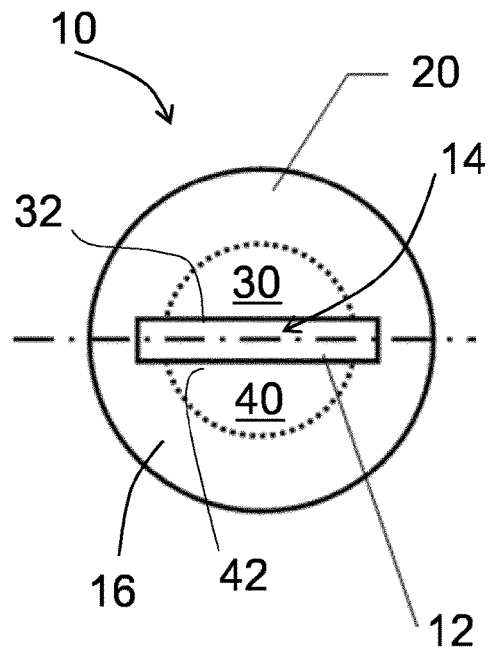
Fig. 1
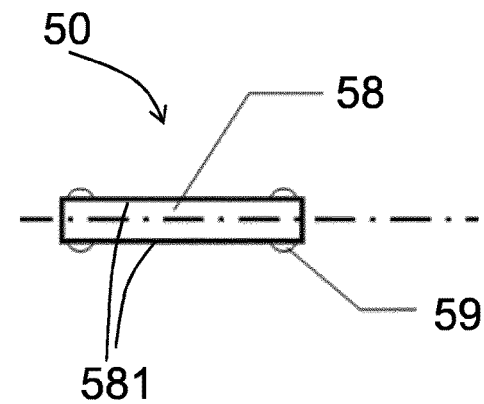
Fig. 2
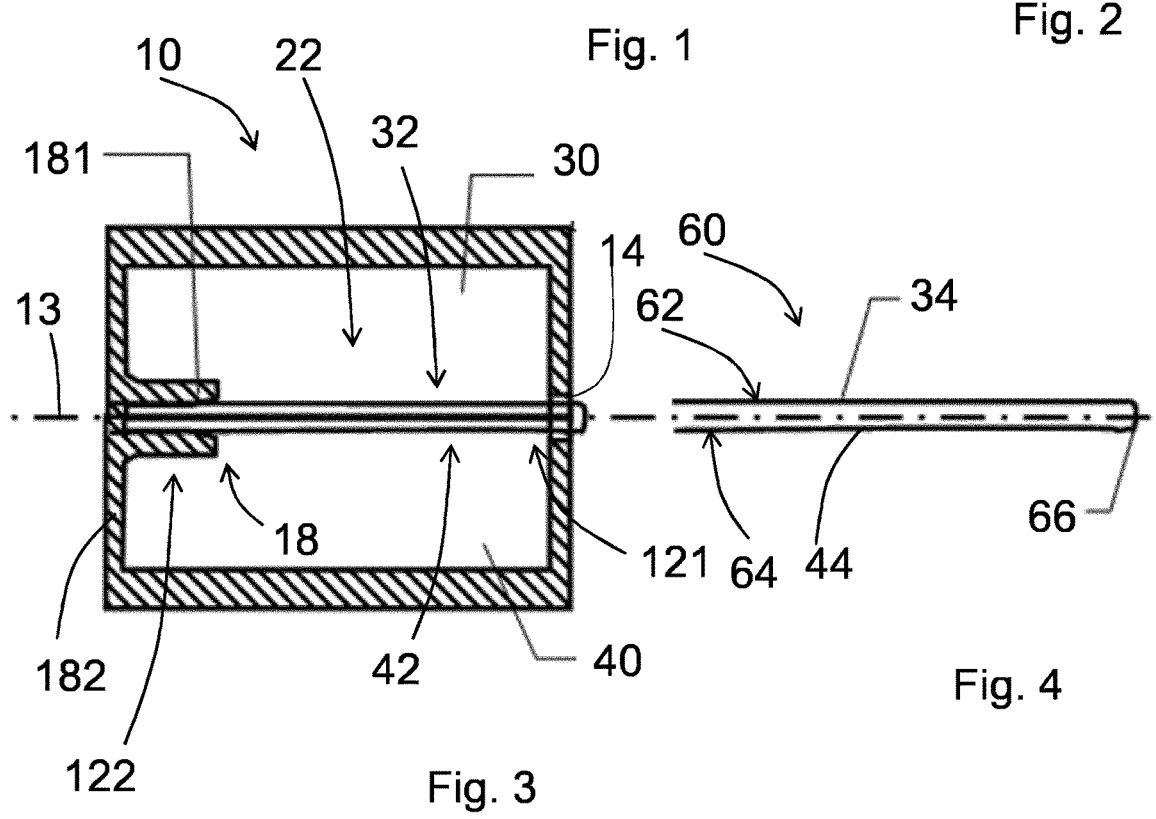
Fig. 3
Fig. 4

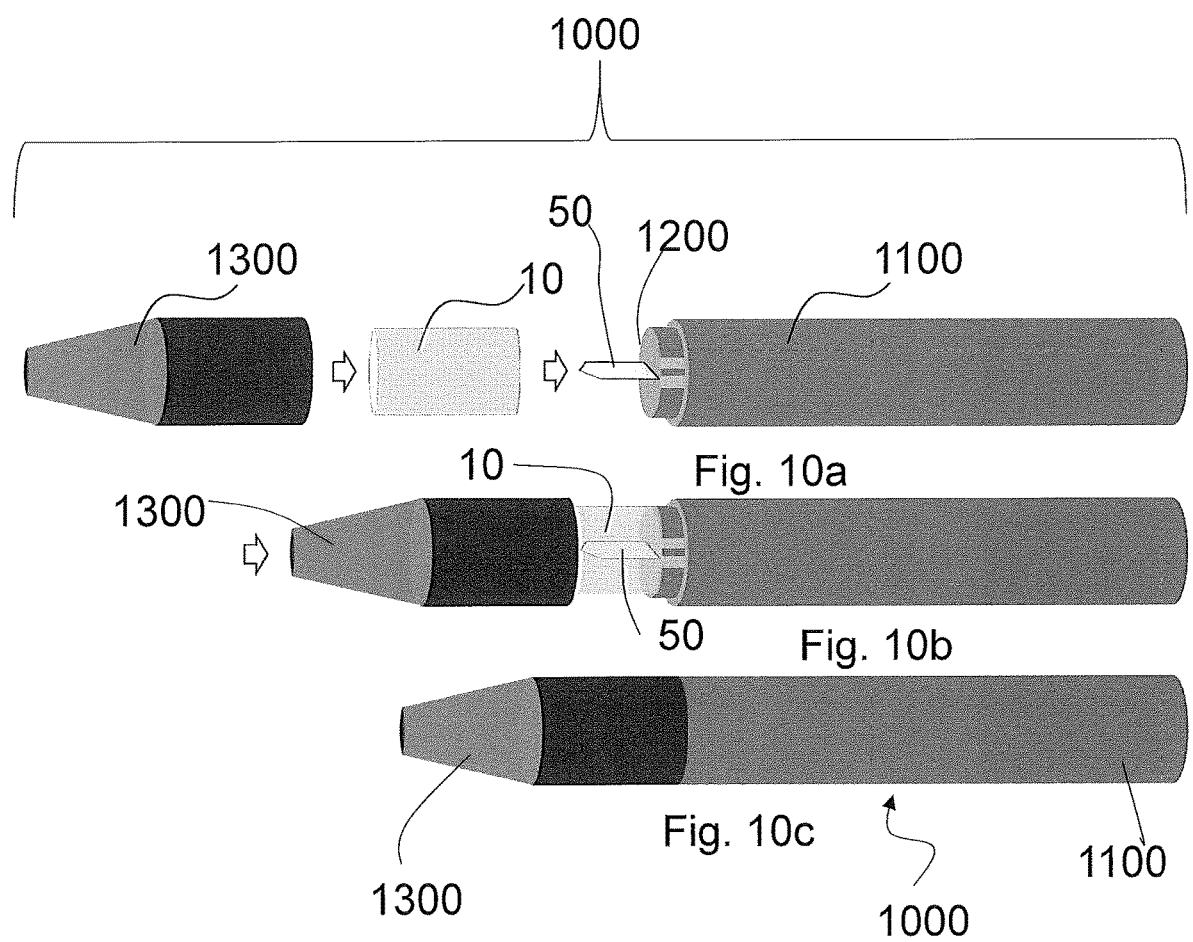

CARTRIDGE AND A SYSTEM FOR AN AEROSOL-FORMING ARTICLE INCLUDING THE CARTRIDGE

This application is a U.S. National Stage Application of International Application No. PCT/EP2016/070589, filed Sep. 1, 2016, which was published in English on Mar. 16, 2017, as International Publication No. WO 2017/042081 A1. International Application No. PCT/EP2016/070589 claims priority to European Application No. 15184800.9 filed Sep. 11, 2015.

The present invention relates to a cartridge including preferably but not necessarily an aerosol-forming substrate and a system including the cartridge to be used in an aerosol-forming article.

So-called "e-cigarettes" and other electrically operated smoking systems that vaporize a liquid nicotine formulation to form an aerosol that is inhaled by a user are known in the art. For example, WO 2009/132793 A1 discloses an electrically heated smoking system comprising a shell and a replaceable mouthpiece wherein the shell comprises an electric power supply and electric circuitry. Electronic cigarettes or vapor inhalers generally use a heater to vaporize liquid nicotine, or other liquid substances. The user inhales on the electronic cigarette drawing ambient air through the electronic cigarette housing. The vapor or mist mixes with the air flow moving through the housing and is inhaled by the user. The liquid nicotine or other substances are generally contained in a replaceable cartridge.

Alternatively, cartridges containing aerosol-forming substrates can be used in aerosol-forming devices for the administration of medicines, which are contained in the cartridge itself.

These cartridges in general include one or more components of the aerosol-forming substrate in one or more separated chambers. The component, often in the liquid form, remains in the chamber of the cartridge due generally to the presence of a film or foil used as a sealant to close the chamber in the cartridge where the component is contained. The film or foil is then ruptured by a blade or similar tool, for example inserted in an opening, so that the component contained in the chamber can flow outside it.

Keeping the cartridge sealed until the blade or other unsealing tool is inserted is important, as otherwise the one or more components located inside the cartridge could react with air or could leak outside the cartridge. Furthermore, in case different components contained in different chambers of the cartridge are used, it is important that these different components are kept separated from each other until or even after the blade is inserted.

WO 2015/038981 describes a programmable smoking cessation system which includes an electronic vaporizing apparatus system, apparatus, nicotine management plan. Methods for the reduction of nicotine consumption based on the nicotine management plan to reduce or eliminate nicotine dependence. The systems, apparatuses and methods described herein utilize a digital processing device in combination with a vapor release mechanism to vaporize and blend nicotine and non-nicotine liquid substances from cartridge chambers to produce vapors configured to reduce nicotine consumption and dependence at a modulated rate over a specified period of time based on the nicotine management plan. The system and apparatus are configurable to track and report data acquired during use and provide feedback to a user and/or a clinical professional.

There is therefore a need for a cartridge, to be used preferably in connection to aerosol-forming articles, which includes a component confined by a sealing—such as a film or foil—to be opened by an external piercer, such as a part of a vaporizer unit, which is at the same time easy to manufacture, includes a secured sealing mechanism which minimizes leakage and is easy to unseal by users. Further, there is a need of a method for opening the cartridge in order to use the sealed component therein included which is simple, quick, and reliable in the sense that it opens the cartridge correctly most of the times so that the component(s) therein contained can flow outside the cartridge itself.

According to a first aspect, the invention relates to a cartridge comprising an outer shell defining an inner volume containing: a first reservoir containing a first component and having a first aperture for the discharge of the first component; a second reservoir containing a second component and having a second aperture for the discharge of the second component; a first removable film impermeable to the first component of a mixture sealing the first aperture; and a second removable film impermeable to the second component sealing the second aperture. Further, the cartridge in its inner volume comprises a seat having an opening in the outer shell and delimiting walls within the inner volume, the first and second apertures being formed in said delimiting walls, the seat being configured to house a piercer of an external component. According to the invention, a portion of the first film or a portion of the second film is protruding from the opening or it faces said opening.

As discussed further below, use of cartridges according to the invention, for example in an aerosol forming article, advantageously allows an easy opening of the reservoirs containing the two components by the user. This opening can be performed either pulling the portion of the first or second removable film protruding from the outer shell, or inserting the piercer into the seat and—during the insertion movement of the piercer—pulling the film by dragging the same so as to open the aperture(s).

The cartridge houses a first and a second reservoirs containing a first and a second components. The first and second component may be the same component divided in two reservoirs. Preferably, the first and second components are preferably two different components. When the first and second components are put in contact, a mixture is formed. The first component, the second component, or the mixture formed by the first and the second components can comprise for example nicotine, or a medicament, or salt particles. The first component and the second component are preferably liquids.

The mixture of the first and the second components is preferably an aerosol-forming substrate, more preferably in a liquid form. The mixture of the first and the second components may be in a gel or a solid form. In case the aerosol-forming substrate is a liquid, the aerosol-forming substrate preferably has physical properties, for example boiling point and vapour pressure, suitable for use in the cartridge to be used in an aerosol-forming device, for example to be properly heated to form an aerosol. If the boiling point is too high, it may not be possible to heat the mixture but, if the boiling point is too low, the mixture may heat too readily. The liquid preferably comprises a tobacco-containing material comprising volatile tobacco flavour compounds which are released from the liquid upon heating. The mixture may comprise a non-tobacco material. The mixture may include aqueous solutions, non-aqueous solvents such as ethanol, plant extracts, nicotine, natural or artificial flavours or any combination of these. Preferably, the mixture further comprises an aerosol former that facilitates the formation of a dense and stable aerosol. Examples of suitable aerosol formers are glycerine and propylene glycol.

The first and second reservoirs may have any desired shape, they may be for example formed as a portion of a sphere or as a portion of a cylinder. Preferably, the first and the second reservoirs are identical to each other and disposed symmetrically on opposite side of a symmetry plane. Each reservoir includes an aperture from which the component contained therein may exit the reservoir.

The first and the second apertures are closed, or sealed, by a respective first and second removable films. The first and second removable films are impermeable to the first and second components, respectively, so that when the first and the second removable film are sealing the first and the second apertures, respectively, no leakage of the first or second component takes place. The first and second removable films could be realized in paper, plastic, metal (such as aluminum) or polymer. The first or the second film or both may include a colaminated foil for example realized in polyethylene/polypropylene/polyethylene terephthalate.

With the term "film", a relatively thin, flexible sheet, regardless of the material in which is formed, is meant. In case the film is made of a metal, it is for example a foil.

The sealing of the first and second removable films on the first and second aperture is realized according to standard techniques and therefore is not further discussed.

The first and the second removable films may be two distinct portions of the same removable film which is preferably wide enough to cover and be sealed in front of both the first and the second apertures, or it may include two different separated films. The first and second removable films may be realized in the same material, or in different materials, depending of the type of components present in the first and second reservoirs, which may have different properties.

The first and second reservoirs are contained in an outer shell that has in its outer surface an opening to access a seat. The seat is preferably longitudinally extended and includes delimiting walls as well as preferably an end wall substantially opposite to the opening. In the delimiting walls, the first and second apertures are realized, covered by the first and second film. For example, the seat could have the shape of a parallelepiped and the first and the second apertures could be realized in two faces of the parallelepiped, preferably opposite to each other. However, any other geometrical shape of the seat is possible as well without modifying the teaching of the present invention. The first and second apertures may face each other.

The seat is adapted to receive an external element, such as a piercer, part of an external component not included in the cartridge. The piercer is inserted in the seat via the opening. The piercer maybe for example part of a vaporizer unit which further comprises a heat source, in order to heat and vaporize the first and second components contained in the first and in the second reservoirs. The cartridge and vaporizer unit are for example part of an aerosol-forming device. Alternatively, the piercer may be connected to a container where the first and second components are mixed and then delivered as a medicine.

A portion of the first or of the second removable film may protrude from the seat through the opening. A portion of the first or of the second removable film may face the opening. The meaning of "face the opening" is that the area defined by the opening is closed at least partially by means of the portion of the first or of the second removable film. In order to enter the seat, a contact with the portion of the first or second removable film facing the opening is made. Therefore, if a portion of the first or second removable film faces the opening, when the piercer is inserted in the seat, it is not possible to avoid contact to the portion of removable film, thus the portion is hit by the piercer.

The invention may allow an easy opening of the cartridge by the user and at the same time it may assure a tightness of the first and second reservoirs avoiding leakage of the components when the piercer is not inserted. The first and second apertures are tightly sealed by the first and second removable film, respectively.

The user may open the cartridge in order to use the same, for example in an aerosol-forming article, by pulling the portion of the first or second removable film which is protruding from the aperture. Pulling the film causes the film to peel off from the aperture and therefore an easy opening of the reservoir is obtained. Alternatively, the piercer of the external component, such as a vaporizer unit, is inserted in the seat via the opening; the first or second film is dragged by the piercer insertion and therefore peeled off from the first or second aperture, opening it. The first or second removable film is dragged by the piercer due to the presence of the portion of the first or second film facing or protruding from the opening on the outer shell which is hit by the piercer in its insertion.

Preferably, the seat defines a first and a second axial end, the first axial end including the opening, and the first or the second removable film is U-shaped having a first and a second arms and a bend portion therebetween, wherein the first arm of the first or second U-shaped film seals the first or the second aperture and the bend portion is located at the first or at the second axial end of the seat. In order to facilitate the peeling off of the first or second removable film from the first or second aperture so as to open the same, either by pulling the portion protruding from the seat or inserting the piercer in the seat, a special geometry of the first or second removable film has been selected. Preferably, the first or second removable film, more preferably both, has a U-shaped form, where a first arm, a second arm and a bend portion therebetween are defined. A first arm of the first film is used to seal the first aperture of the first reservoir. Likewise, preferably the first arm of the second film is used to seal the second aperture of the second reservoir. In this configuration, preferably the apertures are realized in delimiting walls of the seat which are substantially facing each other. The second arm of the first removable film or the second arm of the second removable film is preferably substantially "free", that is, it is not attached to any object or element of the cartridge. The bend portion included between the first and second arm of the first or of the second removable film is preferably located at the first or at the second axial end of the seat. The first axial end of the seat includes the opening, therefore, if the bend portion is located at the first axial end, it either protrudes or faces the opening of the seat of the cartridge. Alternatively, if the bend portion is located at the second axial end opposite to the opening, then the portion protruding or facing the opening is a portion of the second arm of the first or second removable film.

More preferably, the bend portion is located at the second axial end of the seat opposite to the opening and the portion protruding from the opening includes an end portion of the second arm of the first or second U-shaped film.

More preferably, the first and the second removable films are U-shaped, each removable film having a first and a second arm and a bend portion therebetween, wherein the first arm of the first U-shaped film seals the first aperture and the first arm of the second U-shaped film seals the second aperture, the bend portion of the first film and the bend portion of the second film are located at the second axial end of the seat opposite to the opening and the portion protruding from the opening includes an end portion of the second arm of the first U-shaped film and an end portion of the second arm of the second U-shaped film. Both apertures may be opened with a single movement by the user by pulling the protruding end portions of the second arms of the first and second removable films. Pulling the end portions of the second arms of the first and second films implies that a force is exerted on the first arms of the first and of the second removable film directed towards the opening, due to the U-shaped geometry of the removable films. This force causes the first arms of the first and second removable films sealing the first and second apertures to peel off, opening the first and second apertures. The first and second films are pulled out the outer shell of the cartridge. The first and second apertures may face one the other and the first arm of the first removable film and the first arm of the second removable film are preferably substantially parallel to each other.

The cartridge preferably comprises a single U-shaped removable film having a first and a second arms and a bend portion therebetween, wherein said first arm comprises the first removable film sealing the first aperture and the second arm includes the second removable film sealing the second aperture, and wherein said bend portion is protruding from said opening or it faces said opening. A single removable film may seal both the first and the second apertures. This single removable film is preferably U-shaped, and the first arm seals the first aperture while the second arm seals the second aperture. Preferably, the first and the second apertures are facing each other so that the first and the second arm are also facing each other and more preferably are substantially parallel to each other. The bend portion connecting the first and the second arm is preferably protruding or facing the opening of the seat. It is preferred that the film peeling off, that is, the removal of the film from the aperture, takes place by means of the introduction of the piercer into the seat. The piercer hits—when introduced—the bend portion of the removable film and drags it along while moving toward the second axial end of the seat. In this translation, a force directed towards the second axial end of the seat is applied to the first and second arm of the film, therefore peeling off the first and second arms from the first and second apertures with the consequence of opening them.

Preferably, the second axial end of the seat opposite to said opening includes an inner abutment adapted for the abutment of the piercer of the external component. An inner abutment may be realized at the second axial end so that, when the piercer is introduced in the seat via the opening, it can abut on the inner abutment and can be solidly coupled with the cartridge. In case a single U-shaped film is present and its bend part is facing or protruding from the opening and the first and second apertures are opened by peeling off the film by means of the introduction of the piercer in the seat so that the film is pulled by the piercer itself, the bend portion is sandwiched between the tip of the piercer and the inner abutment of the cartridge when the piercer is fully inserted in the seat.

More preferably, said inner abutment includes a slot formed in a wall of the seat. The piercer therefore, when inserted, can be introduced in the slot in order to separate the cartridge in two halves, one including the first reservoir and the second including the second reservoir. This configuration may allow a minimization of the risks of contact between the first and the second components when the first and second removable films are peeled off by the piercer. In case the bend portion is sandwiched between the tip of the piercer and the inner abutment, it is also preferably pinched in the slot, when the latter is present.

According to a second aspect, the invention relates to a system for an aerosol-forming article comprising a cartridge according to the first aspect, wherein the first and second component are part of an aerosol-forming substrate; and a vaporizer unit including a heat source and a piercer connected to the heat source, the piercer being adapted to be inserted within the seat of the cartridge. The system above described is preferably used in combination with an aerosol-forming article. The vaporizing unit, preferably part of the aerosol forming article, is arranged to vaporize an aerosol-forming substrate to form the aerosol. As known to those skilled in the art, an aerosol is a suspension of solid particles or liquid droplets in a gas, such as air. The aerosol-forming article may further comprise a main body, and the cartridge according to the first aspect of the invention is connectable to the main body and the cartridge contains the first and second components which together form the aerosol-forming substrate. The vaporizer unit includes preferably a heater. The heater may heat the aerosol-forming substrate by means of one or more of conduction, convection and radiation. The heater may be an electric heater powered by an electric power supply. The heater may alternatively be powered by a nonelectric power supply, such as a combustible fuel: for example, the heater may comprise a thermally conductive element that is heated by combustion of a gas fuel. The heater may heat the aerosol-forming substrate by means of conduction and may be at least partially in contact with the substrate, or a carrier on which the substrate is deposited. Alternatively, the heat from the heater may be conducted to the substrate by means of an intermediate heat conductive element.

Preferably, the aerosol forming article is electrically operated and the vaporizer unit of the aerosol forming article comprises an electric heater for heating the aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate. The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-, zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E. I. du Pont de Nemours and Company, 1007 Market Street, Wilmington, Del. 19898, United States of America.

The at least one electric heating element may comprise an infra-red heating element, a photonic source or an inductive heating element.

The at least one electric heating element may take any suitable form. For example, the at least one electric heating element may take the form of a heating piercer or blade or heating needles or rods. The at least one heating element may heat the aerosol-forming substrate by means of conduction. The heating element may be at least partially in contact with the aerosol-forming substrate. Alternatively, the heat from the heating element may be conducted to the aerosol-forming substrate by means of a heat conductor.

Preferably, the heat source includes a heating area and the piercer includes a first and a second channel in fluid communication to the first and second aperture, respectively, to transport the first and second components of the aerosol-forming material to the heating area. Preferably, when the piercer includes a first and second channel, the first and second components are in liquid form. The first and second channels may be capillaries in communication with the aerosol-forming substrate when the piercer is inserted in the seat. Preferably, the first and second channels are arranged to be in contact with the first and the second components in the cartridge. In that case, in use, the first and the second components are transferred from the first and the second reservoirs towards the heating area, for example by capillary action. Each channel may comprise a first end and a second end, the first end extending into the first or second reservoir for contact with the first or second component therein and at least one electric heating element is arranged to heat the first or second component at the second end. When the heating element is activated, the liquid at the second end of the channel may be vaporized by the heating element to form the supersaturated vapour. The supersaturated vapour is mixed with and carried in the airflow. During the flow, the vapour condenses to form the aerosol and the aerosol is carried towards the mouth of a user using the aerosol-forming article, for example though an outlet and mouthpiece cover.

Preferably, the piercer has a dimension so as to fill the seat substantially completely, so that fluid communication between the first and the second apertures is impeded by the piercer when inserted. Advantageously, when inserted in the seat, the piercer fills up the seat completely. In this way, also when the first and second apertures are not sealed anymore because the first and second removable films have been peeled off, the first and second components are still not in contact to each other, because the possibility of any contact is hindered by the presence of the piercer occupying all the available space within the seat. In this way, the contact and mixture of the first and second component can be accurately controlled and may take place outside the cartridge.

Preferably, the piercer comprises a tip, said tip being adapted to be inserted in the inner abutment of the seat. In this way, if contact is to be avoided between the first and second components within the outer shell, the insertion of the tip in the inner abutment has the function of "sealing" the outer shell inner volume portion where the first reservoir is present from the outer shell inner volume portion where the second reservoir is present.

Preferably, the piercer includes a flat body and one or more sealing protrusions projecting from the flat body in a direction substantially perpendicular to the flat body, said one or more sealing protrusions abutting onto an outer surface of the first or second reservoir when the piercer is inserted in the seat of the cartridge. Such sealing protrusions are preferably arranged beside the first or second aperture of the first or second reservoir, when the piercer is inserted in the seat of the cartridge. In this way, such sealing protrusions have the function of "sealing" the outer shell inner volume portion where the first reservoir is present from the outer shell inner volume portion where the second reservoir is present, preventing the possibility of any contact between the first and second components also after the first and second removable films have been peeled off.

According to a third aspect, the invention relates to a method for opening a cartridge in an aerosol-forming article, comprising: providing a cartridge according to the first aspect of the invention; pulling the portion of the first or of the second film protruding from the outer shell so as to peel off the first or the second removable film and to open the first or second aperture; and inserting the piercer of a vaporizer unit in the seat. This method is applicable to those cartridges according to the first aspect of the invention where a portion of the first or the second removable film, preferably both, is protruding from the opening of the seat. By pulling the portion of the first or second removable film, the aperture of the reservoir containing the first or second component opens, being the film peeled off by the pulling action, and thus the component therein included can be used. The component can be for example heated by the vaporizer unit in order to form an aerosol.

According to a fourth aspect, the invention relates to a method for opening a cartridge in an aerosol-forming article, comprising: providing a cartridge according to the first aspect of the invention; inserting and pushing the piercer of a vaporizer unit in the opening of the seat so as to push the bend portion of the U-shaped film towards the second axial end of the seat opposite to the opening; abutting a tip of the piercer against the second axial end of the seat opposite to the opening, keeping the bend portion of the U-shaped film between the tip and the second axial end of the seat; peeling off said first or second removable film while inserting the piercer, due to the piercer and consequent first or second removable film translation. In case wherein a U-shaped first or second removable film is present and the bend portion of the film is protruding or facing the opening of the seat, the piercer can be used to peel off the film having such bend portion by the piercer introduction into the seat. The piercer with its tip pushes the bend portion of the film toward the second axial end of the seat due to the sliding of the piercer towards the end of the seat. The first arm of the U-shaped film is therefore pulled towards the second axial end of the seat. At a certain point, due to the continuous applied force, the first arm peels off from the first or second aperture. Preferably, if a single U-shaped film is present, wherein the first arm seals the first aperture and the second arm seals the second aperture, with a single insertion of the piercer, both arms are peeled off and both apertures are opened.

Preferably, the step of inserting and pushing the piercer includes inserting the piercer between the first and the second apertures of the cartridge to hinder fluid communication between the first and the second apertures. A mixture between the first and the second component may therefore be realized outside the cartridge in a controlled manner.

Further advantages of the invention will become apparent from the detailed description thereof with no-limiting reference to the appended drawings:

FIG. 1 is a schematic plant view of a cartridge according to the invention;

FIG. 2 is a schematic plant view of a piercer included in a system for an aerosol-forming article comprising the cartridge of FIG. 1;

FIG. 3 is a schematic lateral view of the cartridge of FIG. 1;

FIG. 4 is a schematic lateral view of a component (U-shaped film) of the cartridge of FIG. 1;

FIGS. 10a-10c are schematic perspective views of a system for an aerosol-forming article according to the invention.

Figure 5:
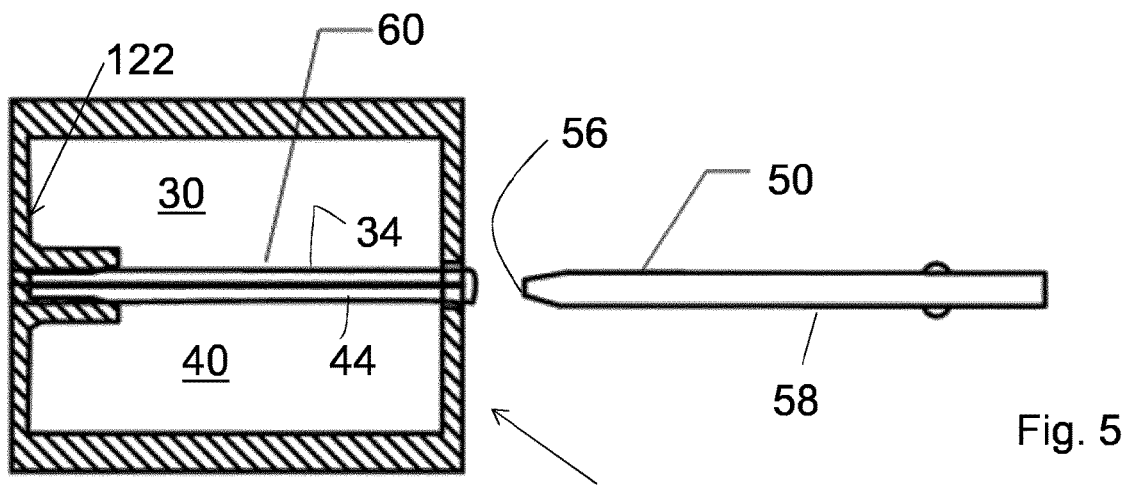
FIGS. 5, 6 and 7 are schematic lateral views of the cartridge of FIG. 1 and of the piercer of FIG. 2, during the approach (FIG. 5) and insertion (FIG. 6, 7) of the piercer into the cartridge.

With initial reference to FIGS. 1-7, a cartridge according to the present invention is represented and indicated with reference number 10.

The cartridge 10 comprises an outer shell 20 having a substantially cylindrical shape. The outer shell 20 defines an inner volume 22 containing a first reservoir 30, containing a first component, and a second reservoir 40, containing a second component. The first and second components may be components, when put in contact, of a mixture for the realization of an aerosol-forming substrate or material.

The first reservoir 30 and the second reservoir 40 have a first aperture 32 for discharge of the first component and a second aperture 42 for discharge of the second component, respectively.

It is possible to adjust how the first and second components will mix by changing how the first and second aperture 32, 42 are located. Furthermore, it is possible to adjust how the first and second components will mix also by choosing the shapes of the first and second reservoir 30, 40.

The cartridge 10 is preferably formed by two facing parts. More preferably, the two facing parts have substantially semi-cylindrical shape and can be clipped or snap fitted together.

Preferably, the two facing parts of the cartridge 10 have—along their outside border—specific coupling shapes (for instance male/female coupling). In this way, guidance for the clipping or snap fitting is provided, as well as will water tightness is assured, from the inside of the cartridge 10 to the outside.

In order to increase the water tightness of the cartridge 10, there could be foam all around the borders of the two facing parts. The foam becomes compressed and watertight when the two facing parts are clipped or snap fitted together.

The first and second reservoir 30, 40 are preferably contained in the two facing parts of the cartridge 10. The first and second reservoir 30, 40 could be or not symmetric to each other.

The cartridge 10 comprises a seat 12 (visible for example in FIG. 2) configured to house a piercer 50 of an external component. Preferably the seat 12 is substantially arranged along a longitudinal axis 13 of the cartridge 10.

The seat 12 comprises an opening 14 in the outer shell 20 and delimiting walls within the inner volume 22. Preferably the opening 14 is arranged on a bottom end portion 16, preferably planar, of the outer shell 20. The first and second apertures 32, 42 are formed in the delimiting walls. In this way, the first and second apertures 32, 42 face toward the inside of the cartridge 10. More preferably, the first and second apertures 32, 42 face each other.

The cartridge 10 further comprises a first removable film 34 which seals the first aperture 32 and a second removable film 44 which seals the second aperture 42. Thanks to the first and second removable film 34, 44, the first and the second reservoir 30, 40 remain closed up to use of the cartridge 10.

The first removable film 34 is impermeable to the first component and the second removable film 44 is impermeable to the second component, in this way sealing the first and the second apertures avoiding leakage of the first and the second components.

Preferably the first removable film 34 and the second removable film 44 are realized in paper, or plastic or polymeric material. Preferably the first removable film 34 and the second removable film 44 are realized in the same material.

According to the invention, a portion of the first film 34 or a portion of the second film 44 is protruding from the opening 14. Alternatively, a portion of the first film 34 or a portion of the second film 44 faces the opening 14.

The seat 12 defines a first and a second axial end 121, 122. The first axial end 121 includes the opening 14. The second axial end 122 of the seat opposite to the opening 14 includes an inner abutment 18 adapted for the abutment of the piercer 50 of the external component.

Preferably, the inner abutment 18 includes a slot 181 formed in a wall 182 of the seat 12.

In the embodiment of the invention shown in FIG. 4, the first film 34 and the second film 44 are formed in a single U-shaped removable film 60. The single U-shaped film 60 has a first and a second arms 62, 64 and a bend portion 66 therebetween. The first arm 62 comprises the first removable film 34 sealing the first aperture 32 and the second arm 64 includes the second removable film 44 sealing the second aperture 42. The bend portion 66 is protruding from the opening 14 or it faces the opening 14.

Figure 8:
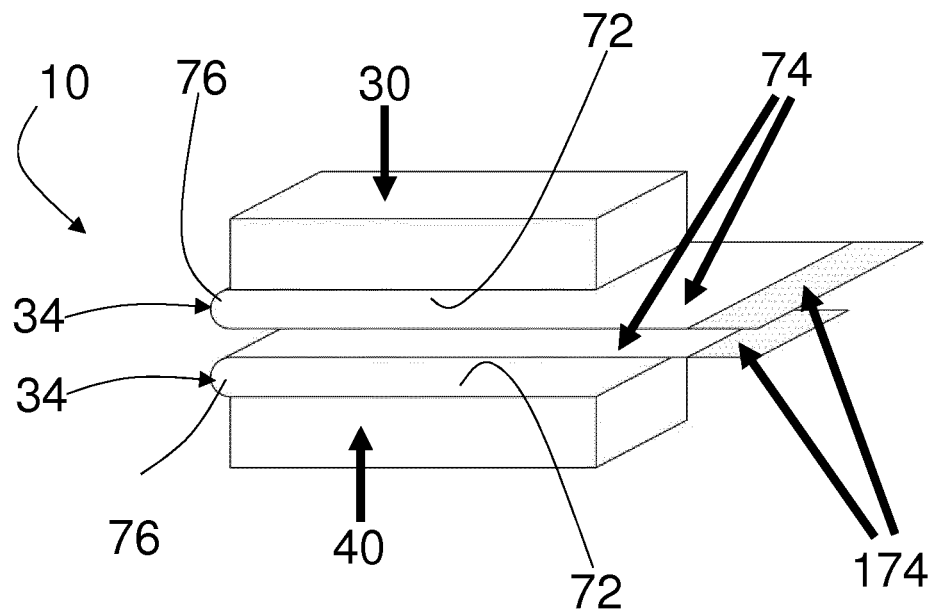
FIG. 8 is a schematic perspective view of another embodiment of a cartridge according to the invention.
Figure 9:
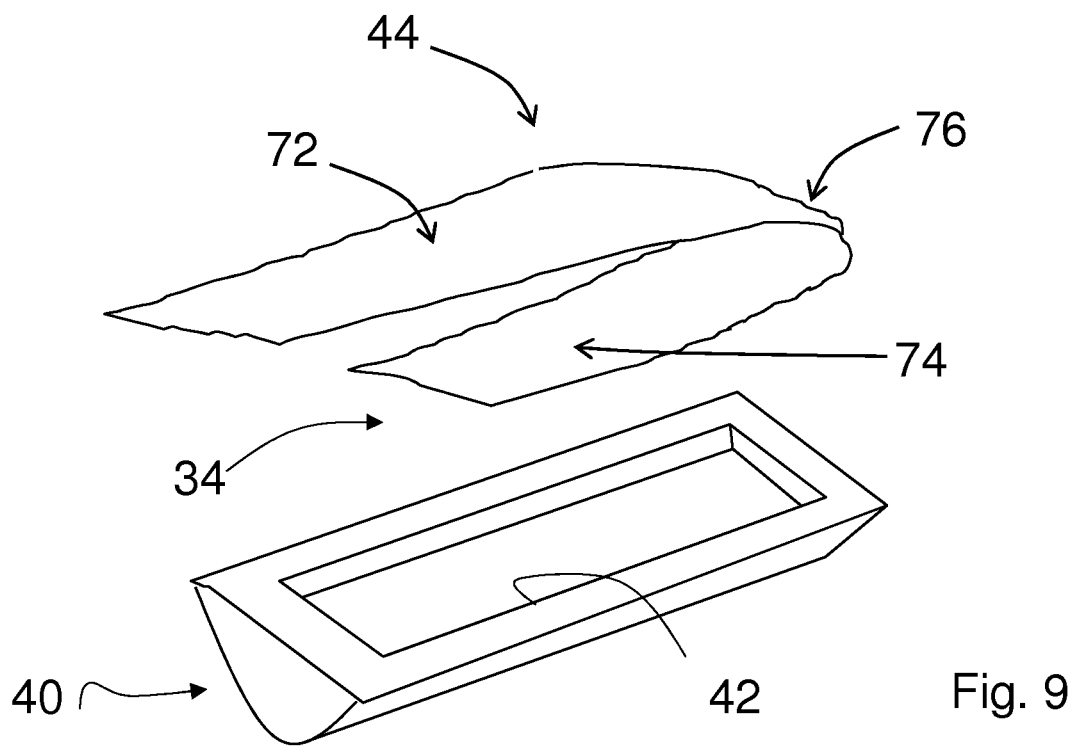
FIG. 9 is a schematic perspective, exploded view of part of the cartridge of FIG. 8.

With reference to FIGS. 8 and 9, another embodiment of the invention is shown, wherein the first and the second removable films 34, 44 separated from each other are U-shaped. Indeed each of the first and second removable films 34, 44 includes a first and a second arms 72, 74 and a bend portion 76 therebetween (in FIG. 9 only the second film 44 is shown). The first arm 72 of the first and second U-shaped films 34, 44 seals the first and the second apertures 32, 42 and the bend portion 76 is located at the first or at the second axial end 121, 122 of the seat 12 (see FIG. 8).

In the case in which the bend portions 76 are located at the second axial end 122 of the seat 12 opposite to the opening 14, the portion protruding from the opening 14 includes an end portion 174 of the second arm 74 of the first and of the second U-shaped films 34, 44 (see FIG. 8).

With reference to FIG. 10a, a system for an aerosol-forming article according to the present invention is represented in a partially disassembled configuration and indicated with reference number 1000.

The system 1000 comprises the cartridge 10 described above, wherein the first and second components form a mixture which is an aerosol-forming substrate, and a vaporizer unit 1100 including a heat source 1200 and the piercer 50.

The piercer 50 is connected to the heat source 1200 and is adapted to be inserted within the seat 12 of the cartridge 10.

The heat source 1200 includes a heating area (not visible). The piercer 50 includes a first and a second channel (not visible) in fluid communication to the first and second aperture 32, 42 of the cartridge 10, respectively, in order to transport the first and second component of the aerosol-forming material to the heating area.

Preferably, the piercer 50 has a dimension so as to fill the seat 12 substantially completely, so that fluid communication between the first and the second aperture 32, 42 of the cartridge 10 is impeded by the piercer 50 when inserted in the seat 12.

Preferably, the piercer 50 comprises a tip 56. The tip 56 is adapted to be inserted in the inner abutment 18 of the seat 12. Preferably, the tip 56 is adapted to be inserted in the slot 181 of the seat 12 (see FIG. 3).

Furthermore, as shown also in FIG. 2, the piercer 50 includes a flat body 58 and sealing protrusions 59 projecting from the flat body 58 in a direction substantially perpendicular to the flat body 58. The sealing protrusions 59 are abutting onto an outer surface of the first or second reservoir 30, 40 when the piercer 50 is inserted in the seat 12 of the cartridge 10.

Preferably, the sealing protrusions 59 are longitudinally extended along the piercer 50.

In the non-limiting example of FIG. 2, the sealing protrusions 59 are four, arranged in pair for each of two opposed flat walls 581 of the flat body 58 of the piercer 50. Preferably, each pair of sealing protrusions 59 is preferably arranged beside the first and second aperture 32, 42 of the first and second reservoir 30, 40, when the piercer 50 is inserted in the seat 12 of the cartridge 10.

Alternatively, instead of the sealing protrusions 59 provided on the piercer 50, sealing element can provided on the cartridge 10, in order to prevent mixing of the first and second component of the first and second reservoir 30, 40 once the piercer 50 is inserted in the seat 12 of the cartridge 10.

The operation for opening the cartridge 10 is as follows.

With cartridges 10 where a portion of the first or the second removable film 34, 44 (included the case wherein the first and the second films 34, 44 are formed in the single U-shaped removable film 60) is protruding from the opening 14 of the seat 12, the user pulls the portion of the first and/or of the second film 34, 44 protruding from the outer shell 20. This portion can be for example an end portion of the second arm of a U-shaped film or the bend portion of a U-shaped film. In this way, the first or the second removable film 34, 44, 60 is easily peeled and the first or second aperture 32, 42 is opened. Then the piercer 50 of the external component, such as of a vaporizer unit 1100, is inserted in the seat 12. In this case, the first and second components of the first and second reservoirs 30, 40 are not prevented to mix before the insertion of the piercer 50.

In the case wherein a U-shaped first or second removable film 34, 44 or the single U-shaped removable film 60 is present and the bend portion 76, 66 of the films 34, 44, 60 is protruding or facing the opening 14 of the seat 12, the piercer 50 itself can be used to peel off the films 34, 44, 60 having such bend portion 76, 66.

Figure 6:
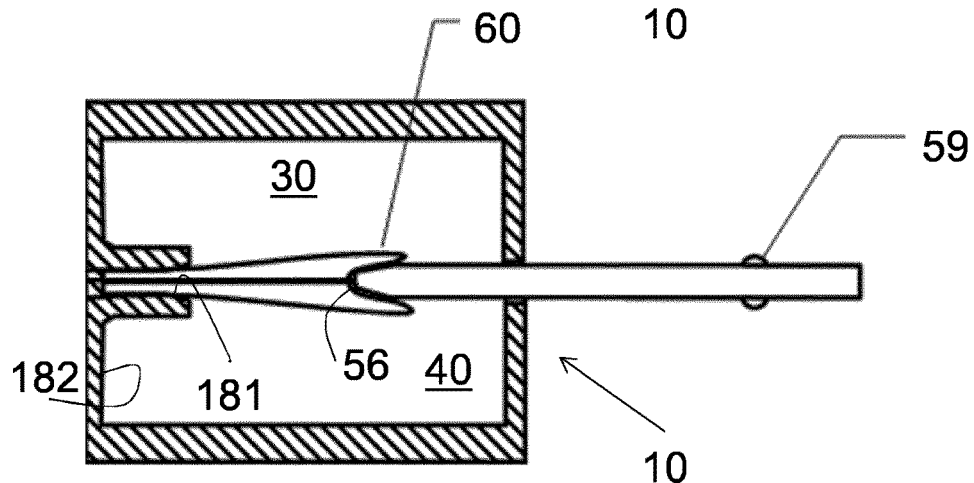
Figure 7:
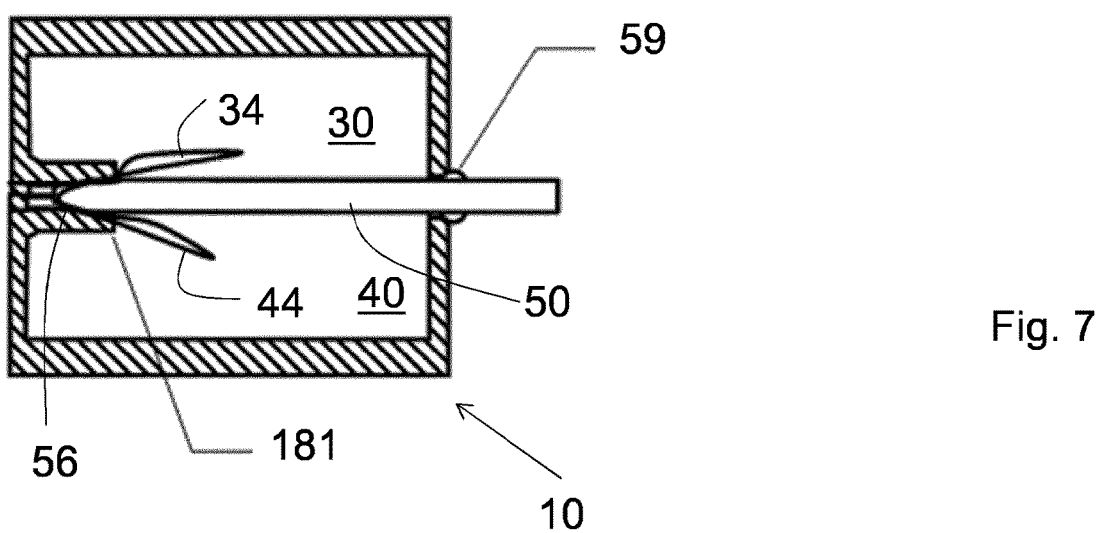

This is obtained by the introduction of the piercer 50 into the seat 12 (see FIGS. 5-7).

FIG. 5 shows the piercer 50 external to the cartridge 10. The cartridge 10 includes a single film 60 sealing both apertures 32, 42. This configuration is substantially analog to the one of FIG. 10*a* where the system 1000 is shown in a partially disassembled configuration.

In FIG. 6, the piercer 50 of the vaporizer unit 1100 is inserted and pushed in the opening 14 of the seat 12 so as to push the bend portion 66 of the U-shaped film 60 towards the second axial end 122 of the seat 12 opposite to the opening 14. In the system 1000, this is obtained introducing the piercer 50 protruding from the vaporizer unit 1100 into the cartridge, as shown by the arrow depicted in FIG. 10*b*.

The tip 56 of the piercer 50 is abutted against the second axial end 122 of the seat 12 opposite to the opening 14. The bend portion 66 of the U-shaped film 60 is kept between the tip 56 and the second axial end 122 of the seat 12. Preferably the bend portion 66 is kept between the tip 56 and the slot 181 of the seat 12. In particular, the bend portion 66 is pinched in the slot 181, while the tip 56 is inserted by interference in the slot 181 (see FIG. 7).

The piercer 50 is preferably provided also with transversal sealing protrusion(s) 59 (in the non-limiting example of FIG. 7, two opposite transversal sealing protrusions 159 are provided, on opposite sides of the piercer 50). The transversal sealing protrusions 159 seal the opening 14 when the tip 56 of the piercer 50 is inserted in the slot 181 (see FIG. 7).

The same method of FIGS. 5-7 can be applied when two separate first and second removable films 34, 44 are present. The first or second film can be peeled off from the first or second aperture 32, 42 while inserting the piercer 50, due to the piercer 50 insertion and the consequent first and/or second removable films 34, 44 translation. Advantageously, an automatic opening of the first and/or second aperture 32, 42 is obtained during insertion of the piercer 50.

Preferably, the piercer 50 with its tip 56 pushes the bend portion 76, 66 of the films 34, 44, 60 toward the second axial end 122 of the seat 12 due to the sliding of the piercer 50 towards the second axial end 122 of the seat 12. The first arm 72, 62 of the U-shaped films 34, 44, 60 is therefore pulled towards the second axial end 122 of the seat 12. At a certain point, due to the continuous applied force, the first arm 72, 62 peels off from the first or second aperture 32, 42. Preferably, in the case of the single U-shaped film 60, with a single insertion of the piercer 50, both the first arm 72 sealing the first aperture 32 and the second arm 74 sealing the second aperture 42 are peeled off and both apertures 32, 42 are opened.

With reference to FIGS. 5-7, during insertion of the piercer 50, the bend portion 66 of the film 60 goes from a U-shape to a W-shape, as the bottom of the U is being pushed by the tip 56 of the piercer 50.

Preferably, the step of inserting and pushing the piercer 50 includes inserting the piercer 50 between the first and the second aperture 32, 42 of the cartridge 10. In this manner fluid communication between the first and the second aperture 32, 42 is hindered and the mixture between the first and the second component is therefore realized outside the cartridge 10 in a controlled manner.

In this case, the first and second components of the first and second reservoir 30, 40 are always kept separated from each other, first by the U-shaped films 34, 44, 60, and then by the inserted piercer 50. Thus, the first and second components are kept separated even during the use of the system 1000.

Advantageously, the system 1000 comprises a mouthpiece 1300 in order to cover the cartridge during use of the system for an aerosol-forming article, as shown in FIG. 10*c*.

The invention claimed is:

1. A cartridge, comprising:
An outer shell defining an inner volume containing:
A first reservoir containing a first component and having a first aperture for discharge of the first component;
a second reservoir containing a second component and having a second aperture for discharge of the second component;
A first removable film impermeable to the first component sealing the first aperture;
A second removable film impermeable to the second component sealing the second aperture;
A seat having an opening in said outer shell and delimiting walls within said inner volume, said first and second apertures being formed in said delimiting walls, the seat being configured to house a piercer of an external component; and
Wherein a portion of the first film or a portion of the second film is protruding from said opening or it faces said opening.

2. The cartridge according to claim 1, wherein the seat defines a first and a second axial ends, the first axial end including said opening, and the first or the second removable film is U-shaped having a first and a second arms and a bend portion therebetween, wherein the first arm of the first or second U-shaped film seals the first or the second aperture and the bend portion is located at the first or at the second axial end of the seat.

3. The cartridge according to claim 2, wherein the bend portion is located at the second axial end of the seat opposite to the opening and the portion protruding from the opening includes an end portion of the second arm of the first or second U-shaped film.

4. The cartridge according to claim 3, wherein the first and the second removable films are U-shaped, each removable film having a first and a second arms and a bend portion therebetween, wherein the first arm of the first U-shaped film seals the first aperture and the first arm of the second U-shaped film seals the second aperture, the bend portion of the first removable film and the bend portion of the second removable film are located at the second axial end of the seat opposite to the opening and the portion protruding from the opening includes an end portion of the second arm of the first U-shaped film and an end portion of the second arm of the second U-shaped film.

5. The cartridge according to claim 2, wherein the first and the second removable films are U-shaped, each removable film having a first and a second arms and a bend portion therebetween, wherein the first arm of the first U-shaped film seals the first aperture and the first arm of the second U-shaped film seals the second aperture, the bend portion of the first removable film and the bend portion of the second removable film are located at the second axial end of the seat opposite to the opening and the portion protruding from the opening includes an end portion of the second arm of the first U-shaped film and an end portion of the second arm of the second U-shaped film.

6. The cartridge according to claim 2, comprising a single U-shaped removable film having a first and a second arms and a bend portion therebetween, wherein said first arm comprises the first removable film sealing the first aperture and the second arm includes the second removable film sealing the second aperture, and wherein said bend portion is protruding from said opening or it faces said opening.

7. A method for opening a cartridge in an aerosol-forming article, comprising:
Providing a cartridge according to claim 6;
Inserting and pushing the piercer of a vaporizer unit in the opening of the seat so as to push the bend portion of the U-shaped film towards the second axial end of the seat opposite to the opening;
Abutting a tip of the piercer against the second axial end of the seat opposite to the opening, keeping the bend portion of the U-shaped film between the tip and the second axial end of the seat;
Peeling off the first or second removable film while inserting the piercer, due to the piercer and consequent first or second removable film translation.

8. Method according to claim 7, wherein the step of inserting and pushing the piercer includes:
Inserting the piercer between the first and the second aperture of the cartridge to hinder fluid communication between the first and the second aperture.

9. The cartridge according to claim 1, wherein the second axial end of the seat opposite to said opening includes an inner abutment adapted for the abutment of the piercer of the external component.

10. The cartridge according to claim 9, wherein said inner abutment includes a slot formed in a wall of the seat.

11. The cartridge according to claim 1, wherein the first removable film or the second removable film is realized in paper, or plastic or polymeric material.

12. A system for an aerosol-forming article comprising:
A cartridge according to claim 1, wherein the first and second component are part of an aerosol-forming substrate; and
A vaporizer unit including a heat source and a piercer connected to the heat source, the piercer being adapted to be inserted within the seat of the cartridge.

13. The system according to claim 12, wherein the heat source includes a heating area and the piercer includes a first and a second channel in fluid communication to the first and second aperture, respectively, to transport the first and second components of the aerosol-forming material to the heating area.

14. The system according to claim 12, wherein the piercer has a dimension so as to fill the seat substantially completely, so that fluid communication between the first and the second aperture is impeded by the piercer when inserted.

15. The system according to claim 12, wherein the piercer comprises a tip, the tip being adapted to be inserted in the inner abutment of the seat.

16. The system according to claim 12, wherein the piercer includes a flat body and one or more sealing protrusions projecting from the flat body in a direction substantially perpendicular to the flat body, the one or more sealing protrusions abutting onto an outer surface of the first or second reservoir when the piercer is inserted in the seat of the cartridge.

17. A method for opening a cartridge in an aerosol-forming article, comprising:
Providing a cartridge according to claim 1;
Pulling the portion of the first or of the second film protruding from the outer shell so as to peel off the first or the second removable film and to open the first or second aperture; and
Inserting the piercer of a vaporizer unit in the seat.

* * * * *